United States Patent [19]

Hagen

[11] 4,433,174

[45] Feb. 21, 1984

[54] PROCESS FOR PREPARATION OF ALPHA, BETA-UNSATURATED ALDEHYDES USING AMS-1B BOROSILICATE CRYSTALLINE MOLECULAR SIEVE

[75] Inventor: Gary P. Hagen, Glen Ellyn, Ill.

[73] Assignee: Standard Oil Company (Indiana), Chicago, Ill.

[21] Appl. No.: 401,548

[22] Filed: Jul. 26, 1982

[51] Int. Cl.³ .............................................. C07C 47/20
[52] U.S. Cl. .................................... 568/459; 568/463; 568/464
[58] Field of Search ................ 568/454, 463, 464, 759

[56] References Cited

U.S. PATENT DOCUMENTS 3,574,703  4/1971  Hagemeyer et al. ............... 568/464

FOREIGN PATENT DOCUMENTS 47-13017  4/1972  Japan ............................... 458/464

Primary Examiner—Werren B. Lone
Attorney, Agent, or Firm—William C. Clarke; William T. McClain; William H. Magidson

[57] ABSTRACT

Alpha, beta-unsaturated aldehydes are prepared by reacting formaldehyde and a reactant aldehyde of formula $RCH_2CHO$ wherein R is a member of the class consisting of -H, -alkyl, -aryl, -aralkyl, -cycloalkyl, and -alkylaryl radicals in the presence of AMS-1B borosilicate crystalline molecular sieve catalyst. Metacrolein is prepared from propionaldehyde and formaldehyde.

18 Claims, No Drawings

PROCESS FOR PREPARATION OF ALPHA, BETA-UNSATURATED ALDEHYDES USING AMS-1B BOROSILICATE CRYSTALLINE MOLECULAR SIEVE

BACKGROUND OF THE INVENTION

This invention relates to the preparation of alpha, beta-unsaturated aldehydes by reacting formaldehyde with a reactant aldehyde of the formula $RCH_2CHO$ wherein R is a member of the class consisting of —H, —alkyl, —aryl, —aralkyl, —cycloalkyl, and —alkylaryl radicals, the number of carbon atoms in R being preferably from 1 to 18.

It is well-known that unsaturated aldehydes can be prepared by condensing two aldehydes over a suitable catalyst. This invention relates to a process for preparing unsaturated aldehydes, e.g., acrolein, methacrolein, ethacrolein and the like, by condensing two aldehydes, one of which is formaldehyde, the other aldehyde of formula $RCH_2CHO$ containing two hydrogens on the alpha carbon, in the presence of a catalyst comprising a borosilicate crystalline molecular sieve, designated as AMS-1B. The catalyst has the following composition in terms of mole ratios of oxides:

$$0.9 \pm 0.2 M_{2/n}O : B_2O_3 : YSiO_2 : ZH_2O$$

wherein M is at least one cation, n is the valence of the cation, Y is a value within the range of 4 to about 600, and Z is a value within the range of 0 to about 160, and providing a specific X-ray diffraction pattern.

Unsaturated aldehydes, such as acrolein, methacrolein, ethacrolein and the like, are widely used for the production of glycerol, polymers and copolymers, pharmaceuticals, herbicides and other compounds of considerable utility. Various processes and catalysts have been proposed for the preparation of unsaturated aldehydes by an aldol-type reaction. Generally, the reaction of the two aldehydes takes place in the vapor or gas phase in the presence of a basic catalyst.

Various catalysts have been proposed for such reaction. For example, U.S. Pat. No. 2,639,295 to Hagemeyer teaches the preparation of unsaturated aldehydes such as acrolein, methacrolein and the like by condensing formaldehyde with aliphatic aldehydes in the presence of an ammonium salt or the salt of a primary or secondary amine. Preferred catalysts are secondary amine hydrogen halides. A molar excess of a second aldehyde in the ratio of usually 1:5 is taught wherein formaldehyde or acetaldehyde is reacted with the second aldehyde to obtain conversions of formaldehyde of 34.0 to 92.5%. U.S. Pat. Nos. 3,573,702 and 3,701,798 to Snapp, et al. teach a process for producing alpha, beta-unsaturated aldehydes which comprises contacting formaldehyde and a saturated aldehyde in the vapor phase in the presence of a solid catalyst comprising a supported rare earth metal oxide of the lanthanide series, the support being any inert material such as alumina or kieselguhr but which is preferably silica gel. A molar ratio of formaldehyde to an excess of the second aldehyde is taught, up to 1:25, in order to ensure maximum conversion of the formaldehyde. Example 10 of Snapp U.S. Pat. Nos. 3,573,702 and 3,701,798 teaches that a 1:3 molar ratio gave formaldehyde conversions of 34 to 45%. U.S. Pat. Nos. 3,574,703; 3,845,106; 3,928,458 to Hagemeyer, et al. teach the preparation of alpha, beta-unsaturated aldehydes by the vapor phase condensation of saturated aldehydes with at least two hydrogen atoms attached to the alpha carbon with formaldehyde in the presence of an unmodified silica gel catalyst. The activity and effectiveness of the catalysts are taught as functions of their pore volume and surface area. A 3:1 ratio of saturated aldehyde to formaldehyde is taught to obtain formaldehyde conversions of 35 to 45%, and selective yields based on formaldehyde consumed ranged from 88 to 94%.

Olefin oxidation processes for preparation of unsaturated aliphatic aldehydes are known. U.S. Pat. No. 3,437,690 to Young, et al. teaches a process for preparing acrolein which comprises reacting in the vapor phase propylene and oxygen in the presence of a catalyst comprising a calcined mixture of an oxide of arsenic, a molybdochromic heteropoly acid and a carrier. The oxide of arsenic can be alone, or together with an oxide of chromium, manganese, iron or boron. Mole ratio of olefin to oxygen can range from 1:0.2 to 1:10, preferably from 1:0.3 to 1:8. Conversions of propylene to acrolein are taught as within the range of from 3.4 to 16.4% with yields based on propylene within the range of 9.4 to 45.2%. U.S. Pat. No. 3,359,309, also to Young, teaches a similar process for olefin oxidation to acrolein using a catalyst comprising an arsenic oxide, a heteropoly acid of molybdenum containing manganese on a carrier. Conversions based on propylene ranged from 5.2 to 18.4%, and yields based on propylene consumed ranged from 14.4 to 61%.

Accordingly, a number of processes using basic catalysts for the condensation of two aldehydes have been taught heretofore. Other processes have been taught for the oxidation of olefins using an oxide of arsenic. However, the processes and catalysts taught heretofore suffer from disadvantages which are greatly minimized in the process of the instant invention. For instance, the processes taught in U.S. Pat. Nos. 2,639,295; 3,574,703; 3,845,106; and 3,928,458 are inferior to the present invented process in that formaldehyde conversions are low when the second aldehyde concentration is low, that a molar ratio of at least 3:1 is required for conversions of 35 to 45%, based on formaldehyde consumed. The processes taught in U.S. Pat. Nos. 3,359,309 and 3,437,690 are also inferior to the process of the instant invention. Conversions of olefin taught in U.S. Pat. Nos. 3,359,309 and 3,437,690 are within the range of from 3.4 to 18.4%.

An object of the present invention is to provide a process for making unsaturated aldehydes from formaldehyde and other aldehydes. A further object is to provide a process for making acrolein. Another object is to provide a process for making methacrolein. Other objects will appear hereinafter.

Quite unexpectedly, it has been found that a catalyst comprising an AMS-1B borosilicate crystalline molecular sieve having the following composition in terms of mole ratios of oxides:

$$0.9 \pm 0.2 M_{2/n}O : B_2O_3 : YSiO_2 : ZH_2O$$

where M is at least one cation, preferably hydrogen, n is the valence of the cation, Y is a value within the range of 4 to about 600, and Z is a value within the range of 0 to about 160, and providing a specific X-ray diffraction pattern, performs in a much superior manner for the present process with respect to conversion and selectivity relative to previously taught catalysts. Whereas previously taught catalyst formulations usually require a basic metal on silica or alumina substrates, the catalyst of the instant invented process is a borosilicate crystalline molecular sieve catalyst. Yield and selectivity are also improved over previously taught catalysts. The improved process has several unexpected results. Whereas previously taught processes result in low formaldehyde-based yields of alpha, beta-unsaturated aldehydes when the ratio of aldehyde to formaldehyde is low, such as 1:1, the aldehyde:formaldehyde ratio for the process of the present invention is 1:1 to 20:1, preferred is 1:1 to 10:1, more preferred is 1:1, with consequent economic advantage. Also, in the olefin process, substantial amounts of other products, mainly acrylic acid, often are formed from the olefin when the olefin oxidation process is used.

SUMMARY OF THE INVENTION

Disclosed is a process for preparing alpha, beta-unsaturated aldehydes by reaction between formaldehyde and a reactant aldehyde of formula $RCH_2CHO$ wherein R is a member of the class consisting of —H, —alkyl, —aryl, —aralkyl, —cycloalkyl, and —alkylaryl radicals, the number of carbon atoms in R being preferably from 1 to 18, in the presence of an AMS-1B borosilicate crystalline molecular sieve catalyst under reactant conditions wherein the reactant aldehyde:formaldehyde ratio is from about 1:1 to 20:1 at a temperature within the range of from about 250° C. to about 430° C.

DETAILS OF THE INVENTION

The process of the instant invention relates to a process for preparing alpha, beta-unsaturated aldehydes by reaction between formaldehyde and a reactant aldehyde of formula $RCH_2CHO$ wherein R is a member of the class consisting of —H, —alkyl, —aryl, —aralkyl, —cycloalkyl, and —alkylaryl radicals, the number of carbon atoms in R being preferably from 1 to 18, in the presence of AMS-1B borosilicate crystalline molecular sieve catalyst. Yield of alpha, beta-unsaturated aldehydes is increased over previously taught processes and production of by-products is minimized. The general method requires the presence of AMS-1B borosilicate crystalline molecular sieve catalyst. Dry formaldehyde, paraformaldehyde, methanolic formaldehyde or trioxane is reacted with an aldehyde of formula $RCH_2CHO$ wherein R is defined as above in the gas phase at a temperature within the range of from about 250° C. to about 430° C.

The present invention relates to a process using a synthetic crystalline molecular sieve material, a crystalline borosilicate, as a catalyst. The family of such crystalline borosilicate materials, which are identified as AMS-1B borosilicates, and which are taught in commonly-assigned U.S. Pat. No. 4,269,813, incorporated herein by reference, has a particular X-ray diffraction pattern. Such crystalline borosilicate can generally be characterized, in terms of the mole ratios of oxides, as follows in Equation I:

$$0.9 \pm 0.2 M_{2/n}O:B_2O_3:YSiO_2:ZH_2O$$

wherein M is at least one cation, n is the valence of the cation, Y is between 4 and about 600, and Z representing the water present in such material is between 0 and about 160, or more.

In another instance, the claimed crystalline borosilicate can be represented in terms of mole ratios of oxides for the crystalline material not yet activated or calcined at high temperatures as follows in Equation II:

$$0.9 \pm 0.2[WR_2O + (1-W)M_{2/n}O]:B_2O_3:YSiO_2:ZH_2O$$

wherein R is an alkylammonium cation, M is at least one cation, n is the valence of the cation, Y is a value between 4 and 600, Z is a value between 0 and about 160, and W is a value greater than 0 and less than 1.

In Equation I, M can represent an alkali-metal cation, an alkaline-earth-metal cation, an ammonium cation, an alkylammonium cation, a hydrogen cation, a catalytically-active-metal cation, or mixtures thereof. In Equation II, M can represent an alkali-metal cation, an alkaline-earth-metal cation, an ammonium cation, a hydrogen cation, a catalytically-active-metal cation, or mixtures thereof.

Advantageously, the value for Y falls within the range of 4 to about 500. Suitably, Y is 4 to about 300; preferably, about 50 to about 160; and more preferably, about 80 to about 120.

Suitably, Z is within the range of 0 to about 40.

The original cation M in the above formulations can be replaced in accordance with techniques well-known in the art, at least in part by ion exchange with other cations. Preferred replacing cations include tetraalkylammonium cations, metal ions, ammonium ions, hydrogen ions, and mixtures of the above. Particularly preferred cations are those which render the AMS-1B crystalline borosilicate catalytically active, especially for hydrocarbon conversion. These materials include hydrogen, rare earth metals of Group IIIB, lanthanum, aluminum, metals of Groups IA, i.e., sodium, potassium, lithium, etc., IIA, i.e., calcium, strontium, barium, etc., and VIII, i.e., iron, cobalt, nickel, etc., of the Periodic Table of Elements found in the 46th Edition of the *Handbook of Chemistry and Physics* published by the Chemical Rubber Company; noble metals, manganese, and other catalytically active materials and metals known to the art. Rare earth metals, lanthanum, sodium and hydrogen are considered especially useful. The catalytically active components can be present anywhere from about 0.05 to about 25 weight percent of the AMS-1B crystalline borosilicate. The form wherein hydrogen replaces the original cation M and n is 1 in the above formulations is designated HAMS-1B. The hydrogen form of the AMS-1B crystalline borosilicate catalyst imparts an acidic character to the catalyst to improve yields of unsaturated aliphatic aldehydes. Divalent or trivalent cations are generally recognized to impart acidic character to molecular sieves, but the hydrogen ion is considered to impart more acidic character.

Embodiments of such borosilicate composition useful in the process of the instant invented process provide an X-ray diffraction pattern comprising the following X-ray diffraction lines:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |

-continued

| d (Å) | Assigned Strength |
|---|---|
| 1.99 ± 0.02 | VW-M | wherein the assigned strengths correspond to the following values of relative peak heights:

| Assigned Strength | Relative Peak Height |
|---|---|
| VW | less than 10 |
| W | 10–19 |
| M | 20–39 |
| MS | 40–70 |
| VS | greater than 70 |

A range of assigned strengths comprises all strengths between the limits shown.

Embodiments of these borosilicates are prepared by the method which comprises: (1) preparing a mixture containing an oxide of silicon, an oxide of boron, a hydroxide of an alkali metal or an alkaline earth metal, an alkylammonium cation or a precursor of an alkylammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization. The hydrogen form can be obtained by ion exchange.

The AMS-1B crystalline borosilicate useful in this invention can be in an unsupported form for use either in a fixed bed or a fluidized bed reactor. The AMS-1B crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. Catalytic compositions can contain about 0.1 wt.% to about 100 wt.% crystalline borosilicate material and preferably contain about 10 wt.% to about 80 wt.% of such material and most preferably contain about 30 wt.% to about 65 wt.% of such material.

Catalytic compositions comprising the crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled, typically by adding a material such as ammonium hydroxide. The resulting gel can be dried and calcined to form a composition in which the crystalline borosilicate and catalytically active metal compond are distributed throughout the matrix material.

Specific details of catalyst preparation are described in U.S. Pat. No. 4,269,813.

It has been found that borosilicate catalysts prepared by the above method are effective in catalyzing the reaction of aldehydes of the formula $RCH_2CHO$ wherein R is defined as hereinbefore and formaldehyde wherein the reactant aldehyde:formaldehyde ratio is from about 1:1 to about 20:1 at a temperature within the range of from about 250° to about 430° C. and contact time is from about 0.1 to about 20 seconds.

The reactant aldehyde is of the formula $RCH_2CHO$, and has at least two hydrogens on the alpha carbon, the number of carbon atoms in R being preferably from 1 to 18. Examples of acetaldehyde, propionaldehyde, n-butyraldehyde, n-valeraldehyde, isovaleraldehyde, n-caproaldehyde, n-heptaldehyde capric and laurel aldehydes, 2-phenylpropanal, 2-p-tolylethanal, 2-cyctopentylethanal, and 2-phenylethanal. For example, acetaldehyde and formaldehyde are reacted to form acrolein, propionaldehyde and formaldehyde to form methacrolein, n-butyraldehyde and formaldehyde to form ethacrolein, etc.

It is essential for the process and catalyst of the instant invention that water in the reactant aldehyde-formaldehyde feed, preferably an aldehyde-trioxane (or gaseous formaldehyde monomer) feed, and in the reactor under operating conditions be maintained at low levels, no greater than a maximum of 8% by weight of the combined weight of the reactant aldehyde-formaldehyde feed, preferably no greater than 4% by weight. Since water is produced as a by-product of the instant reaction, the reaction can be self-deactivating to the extent that higher conversions of the reactant aldehyde-formaldehyde feed to alpha, beta-unsaturated aldehyde cause higher gas phase concentrations of water in the catalyst bed, thus requiring an increased operating temperature which in turn decreases selectivity to unsaturated aldehyde product. Formaldehyde can be used in any suitable dry form such as dry formaldehyde monomer in a gaseous state, paraformaldehyde, methanolic formaldehyde and trioxane. Trioxane pyrolyzes into gaseous formaldehyde in the presence of the acidic form of AMS-1B catalyst.

As indicated in the examples, the novel process of the present invention is carried out to synthesize alpha, beta-unsaturated aldehydes from reactant aldehydes and formaldehyde. The instant invented process is useful in synthesis of methacrolein by the vapor phase reaction of propionaldehyde and formaldehyde. The instant invented process is also useful in synthesizing other unsaturated aldehydes such as acrolein, ethacrolein, etc.

The instant invented process is a single step process for the synthesis of methacrolein which is catalyzed effectively by an AMS-1B borosilicate crystalline molecular sieve catalyst as described herein.

The invented process for synthesis of methacrolein involves the condensation of formaldehyde, preferably as trioxane, with propionaldehyde. Although the mechanism is unknown, the mechanism probably involves initial attack of hydroxy-methyl carbonium ion or its reactive equivalent upon the enol form of the aldehyde.

The reaction occurs at atmospheric pressure in the gas phase when the reactants are passed through the catalyst in the presence of a nitrogen carrier gas at a temperature of 250° C. to 430° C. Reactant pressures of from about 0.5 to 10 atmospheres can be used. A broad range of reactant ratios can be successfully used for this process. For example, when propionaldehyde and trioxane (in mole ratios varying from 2:1 to 1:1 propionaldehyde:available formaldehyde) are allowed to react at a temperature of 300° C. (or 325° C.), yields of methacrolein obtained vary, respectively, from 68–88% based on formaldehyde and from 44–57% based on propionaldehyde. Other ratios, i.e., 20:1 up to 2:1, propionaldehyde to available formaldehyde, can be used but with consequent loss in propionaldehyde-based yields and in propionaldehyde selectivities.

Yield calculations can be based upon either the reactant aldehyde or formaldehyde. For example, propionaldehyde-based yields are calculated as follows:

$$\frac{\text{Moles Methacrolein of Product}}{\text{Moles Propionaldehyde in Feed}} \times 100 = \text{Yield}$$

Formaldehyde-based yields are calculated as follows:

$$\frac{\text{Moles Methacrolein of Product}}{\text{Moles Formaldehyde in Feed}} \times 100 = \text{Yield}$$

Propionaldehyde selectivity is calculated as follows:

$$\frac{\text{Moles Methacrolein of Product}}{\text{Moles Propionaldehyde Reacted}} \times 100 = \text{Propionaldehyde Selectivity}$$

Formaldehyde selectivity is calculated similarly.

In the following examples the percent of total aldehyde observed in the product mixture (either as unreacted propionaldehyde, as methacrolein or as 2-methyl-2-pentenal, a by-product of the reaction) varies from 94–100%, depending on the reactant ratios, reaction conditions, and age of the catalyst. The compound, 2-methyl-2-pentenal, is the aldol condensation-dehydration product of propionaldehyde, and it is formed in highest yields (up to 7%) under conditions of high temperature, high contact times, and high mole ratios of propionaldehyde to formaldehyde in the feed. Under opposing conditions, however, methacrolein is formed in very high yield and with high selectivity. For example, when a feed containing a 2:1 mole ratio of propionaldehyde to formaldehyde (as trioxane) was passed through the reactor at 300° C. (SPR=0.108 ml/min, $N_2$ carrier rate=6 ml/min) at 44.2% yield (based on propionaldehyde, 50% = theoretical maximum) of methacrolein was obtained at 50.9% conversion of propionaldehyde (50% = theoretical maximum) with 86.8% selectivity based on propionaldehyde and at least 88.4% selectivity based on formaldehyde (88.4=% yield of methacrolein based on trioxane).

Catalytic efficiency was calculated at 1.32 gms methacrolein/gm. cat-hr. The selectivity for 2-methyl-2-pentenal was 4.2% based on propionaldehyde. A significant quantity of this component (about 8% yield) is also formed when a propionaldehyde blank is run through the reactor under the experimental conditions described above. Although aldol condensations are typically best catalyzed by base in homogeneous systems, they are also well-known to occur via catalysis with acid.

Further improved selectivity based on propionaldehyde, as described in the following, was obtained with feed containing a 1:1 mole ratio of propionaldehyde to formaldehyde. The example was run under conditions as described above except a solution containing a 1:1 mole ratio of propionaldehyde to formaldehye was utilized as feed. The yield of methacrolein was 56.6% at 57.3% conversion of propionaldehyde with 98.4% selectivity for methacrolein based on propionaldehyde. Selectivity for 2-methyl-2-pentenal was only 1.9%.

Under these conditions a small amount (1.1% yield based on propionaldehyde) of this by-product was formed. The crossed aldol reaction competes against the homoaldol reaction for catalytically active sites, possibly due to the steric constraints placed on the latter process by the relatively greater bulk of the transition state leading to the formation of 3-hydroxy-2-methyl-2-pentenal and/or by the size of the micropores within the molecular sieve framework.

The invention will be illustrated by reference to the following specific examples.

EXAMPLE I

The reactor consisted of a quartz tube fitted with a thermocouple through the center of the tube to measure and control temperatures. Inlets were provided at the top of the reactor for the carrier gas stream and feed materials. The catalyst bed was positioned in the reactor by an inert support material. Product was removed at the bottom of the quartz tube. Heat was supplied by an electric tube furnace.

A solution of propionaldehyde (10.0 ml, 8.05 gms, 0.1386 moles) and trioxane (2.081 gms, 0.0693 moles) was prepared, and the total solution volume was measured at 12.0 ml. The solution was drawn into a syringe which was then attached to a syringe pump and connected to a septum mounted near the top of the reactor with a long stainless steel needle. The reactor was loaded with 1.00 gms of alumina-supported HAMS-1B catalyst (50 wt. % HAMS-1B and 50 wt. % alumina), and the catalyst bed was then brought to a temperature of 300° C. under a stream of nitrogen gas flowing at a rate of 6.0 ml/min. After a 1 ml pre-run was collected and drained, a 4.0 ml portion of the solution was allowed to pass through the reactor at a rate of 0.108 ml/min. The clear colorless product was collected in a receiver and analyzed by quantitative G-C analysis (SP 1200 column). It was found to contain 1.43 gms (88% yield based on trioxane) of methacrolein and 1.32 gms of unreacted propionic acid.

EXAMPLE II

In the procedure of Example I, a feed solution containing a 1:1 mole ratio of propionaldehyde (propanal) to formaldehyde (as trioxane) was reacted in the presence of alumina-supported HAMS-1B catalyst (50 wt. % HAMS-1B and 50 wt. % alumina). A summary comparison of conversions, yields, selectivities, and efficiencies for Examples I and II are in Table I.

TABLE I

| Effect of Mole Ratios of Reactants on Yield | | |
|---|---|---|
| | Example I Run No. 137 2:1 Prop:Form 2.2 sec. cont. time | Example II Run No. 144 1:1 Prop:Form 1.7 sec. cont. time |
| % Conv. Propanal | 50.9 | 57.5 |
| % Yield Methacrolein | | |
| Based on Propanal | 44.2 | 56.6 |
| Based on Trioxane | 88.4 | 56.6 |
| % Yield MEA[(1)] | | |
| Based on Propanal | 2.1 | 1.1 |
| % Sel[(2)] for Methacrolein | 86.8 | 98.4 |
| For MEA | 4.2 | 1.9 |
| % Total Propanal Bal (Propanal + Methacrolein + MEA) | 95.4 | 100.2 |

TABLE I-continued

Effect of Mole Ratios of Reactants on Yield

|  | Example I Run No. 137 2:1 Prop:Form 2.2 sec. cont. time | Example II Run No. 144 1:1 Prop:Form 1.7 sec. cont. time |
|---|---|---|
| Efficiency: $\frac{\text{gms Methacrolein}}{\text{gms cat-hr}}$ | 1.32 | 1.75 |

Notes:
(1)MEA = α-methyl-beta-ethylacrolein = 2-methyl-2-pentenal.
(2)Based on Propanal.
Conditions:
HAMS-1B catalyst (50 wt. % HAMS-1B and 50 wt. % $Al_2O_3$)
300° C. catalyst bed temperature
.108 ml/min syringe pump rate
Mole ratios and contact times as indicated The above data illustrate the improved results obtained with a 1:1 mole ratio of reactants.

What is claimed is:

1. A process for the preparation of alpha, beta-unsaturated aldehydes by reacting formaldehyde with a reactant aldehyde of formula $RCH_2CHO$ wherein R is a member of the class consisting of —H, —alkyl, —aryl, —aralkyl, —cycloalkyl, and —alkylaryl radicals, in the presence of AMS-1B borosilicate crystalline molecular sieve catalyst under reaction conditions wherein the reactant aldehyde:formaldehyde mole ratio is from about 1:1 to 20:1 at a temperature within the range of from about 250° C. to about 430° C.

2. The process of claim 1 wherein said AMS-1B catalyst composition is the hydrogen form AMS-1B.

3. The process of claim 2 wherein hydrogen of hydrogen form of AMS-1B is replaced by a member of the class consisting of a rare earth metal, lanthanum and sodium.

4. The process of claim 1 wherein said formaldehyde is selected from the group consisting of dry formaldehyde monomer in a gaseous state, paraformaldehyde, methanolic formaldehyde and trioxane.

5. The process of claim 1 wherein said formaldehyde is trioxane.

6. The process of claim 1 wherein said mole ratio of said reactant aldehyde to formaldehyde is within the range of 10:1 to 1:1, reactant aldehyde to formaldehyde.

7. The process of claim 1 wherein mole ratio of said reactant aldehyde to formaldehyde is 1:1.

8. The process of claim 1 wherein R of said formula $RCH_2CHO$ contains from 1 to 18 carbon atoms.

9. The process of claim 1 wherein said reactant aldehyde is selected from the group consisting of acetaldehyde, propionaldehyde, n-butyraldehyde, n-valeraldehyde, isovaleraldehyde, n-caproaldehyde, n-heptaldehyde, capric aldehyde, laurel aldehyde, 2-phenylpropanol, 2-p-tolylethanal, 2-cyclopentylethanal and 2-phenylethanal.

10. The process of claim 1 wherein said reactant aldehyde is acetaldehyde.

11. The process of claim 1 wherein said reactant aldehyde is propionaldehyde.

12. The process of claim 1 wherein said temperature is within the range of from about 275° C. to 350° C.

13. The process of claim 1 wherein water content of said formaldehyde and said reactant aldehyde is no greater than about 8% by weight.

14. The process of claim 1 wherein water content of said formaldehyde and said reactant aldehyde is no greater than about 4% by weight.

15. The process of claim 1 wherein said AMS-1B borosilicate crystalline molecular sieve composition is incorporated within an alumina or silica-alumina matrix.

16. The process of claim 15 wherein said AMS-1B borosilicate crystalline content in said matrix ranges from about 10 to 80 wt.%.

17. The process of claim 15 wherein said AMS-1B borosilicate crystalline content in the matrix ranges from about 30 to 65 wt.%.

18. The process of claim 1 wherein said AMS-1B borosilicate crystalline molecular sieve composition is unsupported.

* * * * *